United States Patent [19]

Schuss et al.

[11] 4,255,143

[45] Mar. 10, 1981

[54] DEVICE FOR RELEASABLY CONNECTING TWO PARTS OF A DENTAL HANDPIECE TOGETHER

[75] Inventors: Werner Schuss, Heppenheim; Hans J. Klose, Hemsbach; Hermann Landgraf, Heppenheim, all of Fed. Rep. of Germany

[73] Assignee: Siemens Aktiengesellschaft, Berlin & Munich, Fed. Rep. of Germany

[21] Appl. No.: 104,980

[22] Filed: Dec. 18, 1979

[30] Foreign Application Priority Data

Dec. 22, 1978 [DE] Fed. Rep. of Germany ....... 2855682

[51] Int. Cl.³ ............................................... A61C 1/08
[52] U.S. Cl. ..................................... 433/126; 403/316
[58] Field of Search ............... 433/105, 130, 126, 133, 433/146; 408/103; 403/316, 317, 327, 349

[56] References Cited

U.S. PATENT DOCUMENTS

| 1,743,241 | 1/1930 | Schmidt | 403/327 |
|---|---|---|---|
| 1,903,445 | 4/1933 | Ernst | 403/316 |
| 2,284,180 | 5/1942 | Thomas | 403/317 |
| 2,942,903 | 6/1960 | Giladett | 403/317 |
| 3,229,369 | 1/1966 | Hoffmeister | 433/133 |
| 3,647,248 | 3/1972 | Ferris et al. | 403/316 |
| 3,830,579 | 8/1974 | Roe | 433/126 |
| 3,909,946 | 10/1975 | Watanabe | 433/126 |
| 4,071,029 | 1/1978 | Richmond et al. | 433/133 |
| 4,182,558 | 1/1980 | Matsuo | 403/316 |

FOREIGN PATENT DOCUMENTS

| 519472 | 2/1931 | Fed. Rep. of Germany | 433/130 |
|---|---|---|---|
| 1766598 | 6/1973 | Fed. Rep. of Germany | 433/126 |

Primary Examiner—Gene Mancene
Assistant Examiner—John J. Wilson
Attorney, Agent, or Firm—Hill, Van Santen, Steadman, Chiara & Simpson

[57] ABSTRACT

A device for releasably connecting two parts together characterized by a projection on one part slideably received in a socket or recess of another part to prevent twisting and to guide the two parts as they begin at connection until stop surfaces abut to define the final connecting position and a connecting mechanism having at least one pair of connecting elements mounted on the parts with one connecting element of the pair having an engagement surface for engaging the other element of the pair and being mounted for rotation on the one part with the engagement surface moving in an arc between an unlocked position to a lock position and the mechanism includes a resilient member acting on the one element to urge the engagement surface along the arc at least during the last part of travel towards the lock position so that two parts are held in a final connecting position by the resilient element acting on the one element.

13 Claims, 7 Drawing Figures

DEVICE FOR RELEASABLY CONNECTING TWO PARTS OF A DENTAL HANDPIECE TOGETHER

BACKGROUND OF THE INVENTION

The present invention is directed to a device for releasably connecting two parts of a dental handpiece together which device enables a quick connection and disconnection of the parts without the assistance of tools and can be used for connecting a head piece to the grip section or for connecting a dental handpiece part to a hose mount or other parts.

In the dental handpiece disclosed in German A.S. 17 66 598, a connecting device includes an annular groove arranged in one of the handpiece parts which receives a radially removable spring loaded pin provided on the other part. In this manner, one of the handpiece parts is protected against inadvertent axial slippage but can be turned around the longitudinal axis. Since a certain axial travel must be had for the engagement of the pin into the annular groove, the device does not provide a friction-type locking together of the two parts. Moreover, the actuation button or handle for unlocking the pin projects radially from the handpiece and can be disruptive.

An axial friction-type locking of the handpiece parts is known and is provided in the form of bayonet catches or joints as disclosed in German A.S. 12 19 170. However, in this type of connection, a twisting of the two handpiece parts with respect to one another is necessary. However, a twisting of the handpiece parts is not always desireable particularly in dental handpiece and angled handpieces which have cooling agent lines incorporated therein. Since one would need to provide flat casket rings at the connecting ends for the cooling lines and a relatively high compression force is required on these casket rings in order to seal the cooling line connections, a bayonet type friction locking device is not desireable in a dental handpiece having cooling lines.

SUMMARY OF THE INVENTION

The present invention is directed to providing a device for releasably connecting two parts of a dental handpiece which can be axially connected to one another and which device insures axial bracing of the two parts when they are connected to one another without having an excess stroke or axial movement and a twisting of the two parts.

The present invention accomplishes these tasks by providing a device for releasably connecting two dental parts of a dental handpiece together. The device comprises coacting means being provided on the two parts for preventing twisting between said parts and for guiding said parts on a path from a beginning of a connection until stop surfaces of said parts abut to define a final connecting position, said coacting means having at least one axial guidance surface; and connecting means for releasably holding the two parts together in the final connecting position including at least one pair of coacting connecting elements mounted on said parts, one connecting element of each pair having an engagement surface for engaging the other element of the pair and being mounted for rotation on one part with the engagement surface moving in an arc between a disconnected or unlocked position and a locked or connected position at which the two parts are in the final connecting position and said connecting means including resilient means for each pair of elements acting on said one element to urge said engagement surface along said arc at least during the last part of travel towards the locked position so that said two parts are held in the final connecting position by the resilient means acting on the one element of the connecting means.

The coaction between the resilient means which can be a spring bolt and the connecting element is such that an over center relationship can occur with the resilient means initially opposing movement of the engagement surface from the disconnected position and then aiding movement to the final connecting position. It is also possible that the relationship of the resilient means to the element is such that the resilient means will urge the element to move the engagement surface along its entire path from the disconnected position to the connected position.

In one embodiment of the invention, the one element is a pin mounted on a disc or plate which plate is mounted for rotation around an eccentric axis to the pin and the disc has edges engaged by the resilient means to initially oppose rotation and then finally urging rotation of the pin around the mounting axis. The other element comprises a slot having surfaces that urge the pin to rotate against the force of the spring and which surfaces extend at an acute angle to the axis of the part.

In another embodiment, the one element is formed by a pair of levers, which are mounted by resilient spring arms with their end surfaces in engagement between the mounting points and have a recess at the engaged end surface to form an engagement surface for receiving a pin fixed to the other part. Initial rotation of the levers is opposed until the pin has moved a sufficient distance to have an over center relationship to the resilient means which are preferably formed by the spring arms extending from the parts.

DESCRIPTION OF THE PREFERRED EMBODIMENTS

Figure 1:
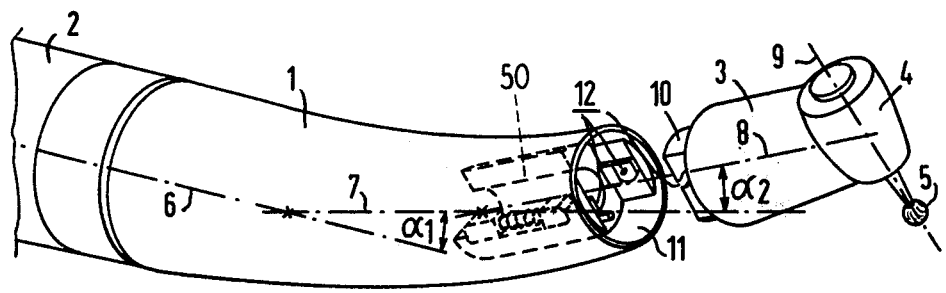
FIG. 1 is an isometric view of a pair of dental handpiece parts in a disconnected position.

The principles of the present invention are particularly useful in a connecting device 12 in FIG. 1 for a dental handpiece. As illustrated, the dental handpiece has a grip section 1, which has one end that is connected to a drive motor part 2. The opposite end of the grip section 1 will be connected to a head part 3. The head part 3 contains a housing 4, which has a socket for mounting a tool 5 for rotation on an axis 9. In order to rotate the socket and tool 5 on the axis 9, the grip section and head part are provided with a drive train of drive shaft section, which for the sake of clarity in the drawings are shown by axes 6, 7 and 8. The axes 6–8 are arranged to be inclined with respect to one another with an angle $\alpha_1$ extending between the intersection of the axis 6 and the axis 7 and the angle $\alpha_2$ between the axis 7 and the axis 8. If desired, the various drive shaft sections may be provided with spherical gear arrangements to enable either a reduction or a stepping of the ratio of rotation between two sections.

The head part 3 on an end facing the grip section 1 is provided with a guidance and centering projection 10 which has planar side surface 15 and will fit into a corresponding recess 11 of the grip section 1. The projection 10 and the recess 11 form coacting means for preventing twisting between the grip section or part 1 and the head part 3 and also coact to axially guide the part 3 as it is being inserted into the recess 11 to move along the axis 8. The device 12 will connect the two handpiece parts 1 and 3 to one another with a friction-type lock when the head part 3 is put in its place.

Figure 2:
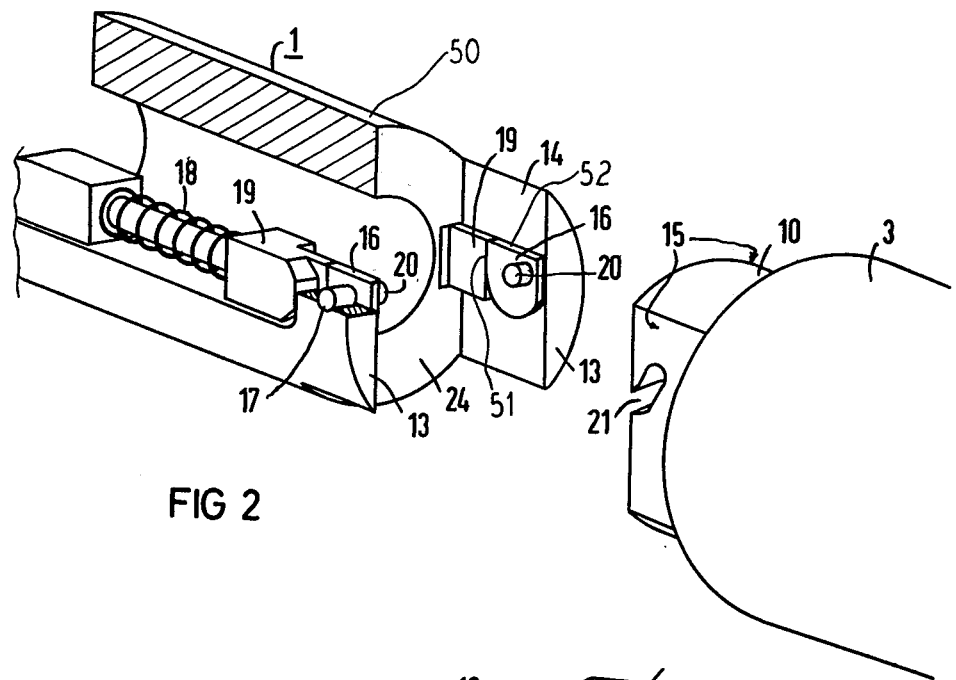
FIG. 2 is an isometric view of two dental handpiece parts with portions broken away for purposes of illustration in a disconnected position.

An embodiment of the device for releasably connecting is illustrated in FIG. 2 and the grip section 1 has the outer sleeve removed so that only a portion 50 is present. The portion 50 has a pair of side extension 13 which extend from the surface 24 and have planar side surfaces 14 which correspond to the planar surface 15 of the projection 10 when the head part 3 is placed. These planar surfaces 14 and 15 act as guiding surfaces for the coacting means. Thus, when the head part 3 is received in the grip section, a precise axial guidance of the part 3 in the portion 50 of the grip sleeve is obtained without twisting.

Figure 4:
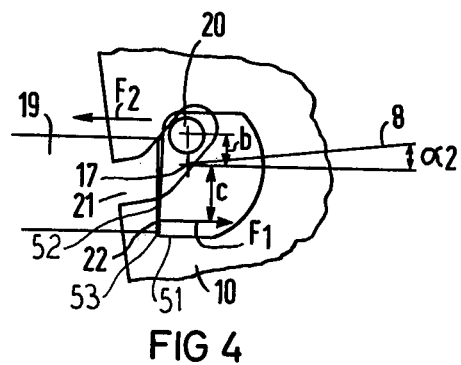
FIG. 4 is a diagrammatic view similar to FIG. 3 showing the coupling elements in a connected or locked position.

To form the connection, a connecting element comprises a plate or disc 16 which is mounted on each of the extensions 13 by the axle 17. Thus, the disc is free to rotate in a plane substantially parallel to the surface 14. Each of the discs 16 is acted on by a resilient means which is illustrated as a thrust bolt 19, which will be moved parallel to the axis of the portion 50 by the force of a compression spring 18. As illustrated, the thrust bolt 19 engages a narrow surface 51 of the disc 16 and the surface 51 intersects a second narrow surface 52 at a corner or high point 53. Each of the discs 16 is provided with a guidance pin or peg 20 which forms an engagement surface and projects inwardly from the disc. The pin, as best illustrated in FIG. 4, is offset by a distance b from the center of the axle 17 so that the axle eccentrically mounts the pin and allows it to rotate in an arc. Because the disc has surfaces such as 51 and 52 which are engaged by the bolt 19 during rotation it becomes a two sided lever with a pivot mounting formed by the axle 17.

The second element of the pair of elements of the connecting means is a slot 21, which is formed in the wall of the projection 10. Each of the slots 21 (FIG. 3) has a first segment 21a which extends parallel to the drive shaft axis 8 and is thus at an angle $\alpha_2$ to the axis 7 on which the bolt 19 moves. A second portion 21b of the slot 21 extends at an acute angle $\alpha_3$ to the axis 8.

Figure 3:
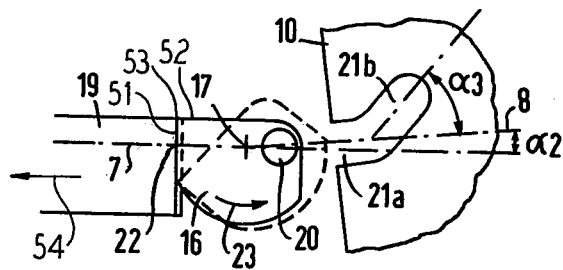
FIG. 3 is a side view schematically illustrating the connecting element while in a disconnected position.

When the head part is pushed onto the grip sleeve 1, the section 21a of each slot will receive the peg 20 during the first portion of movement. In this unlocked position, the thrust bolt 19 exerts no tilting movement on the disc 16 because it is squarely received on the surface 51 as best illustrated in FIG. 3. When the two handpiece parts are moved axially towards one another, the peg which is received in the slot 21 enters the segment 21b where the sides of the slot will rotate the disc 16 around its axle 17 in the direction of arrow 23. This initial movement will push the stop bolt 19 in the direction of arrow 54 against the pressure of the spring 18 or until a corner or high point 53 moves through an over center path so that the spring of the bolt 19 can move in a direction opposite to the arrow 54 to assist in rotating the pin 20 to the position illustrated in FIG. 4 which is the connecting or locked position.

As illustrated by the arrows in FIG. 4, a force a $F_2$ is transferred by the pin 20 to the edge of the slot segment 21b to hold the members in the final connecting position. In view of the fact that the end surfaces of the bolt 19 engages the surface 52 of the plate or disc 16 at a point 22, the force $F_1$ exerted by the bolt 19 acts at a distance c from the center of the axle 17. Therefore, the force equation is $F_1 \cdot c = F_2 \cdot b$. As illustrated in FIG. 4, because the pin 20 will transmit the force $F_2$ to an upper part of the slot segment 21b, the two handpiece parts 1 and 3 are automatically connected to each other by the friction-type lock and are held in the final connection position. It should be noted that the pin 20 has a slight amount of play between the lower and upper edges slot segment 21b. The two parts will continue to move together until either a stop surface formed on the extensions 13 engages a stop surface on the part 3 or the end of the projection 10 engages the stop surface of the rear end surface 24 of the portion 50 of the grip sleeve 1.

For unlocking the two handpiece parts, the head part 3 need only be pulled off in an axial direction against the force $F_2$. Thus, the peg 20, which is moving in the slot 21, will turn the disc on the axle 17 against the force $f_1$ of the spring until the corner 53 passes through the over centered position.

The disc 16 can also be designed in such a manner that when the head part 3 is initially placed on the grip sleeve 1, the spring bolt 19 will initially continuously urge the two parts towards the final connecting position illustrated in FIG. 4. This can be achieved by shaping the edge surfaces such as 51 and 52 into a desired cam surface.

Figure 5:
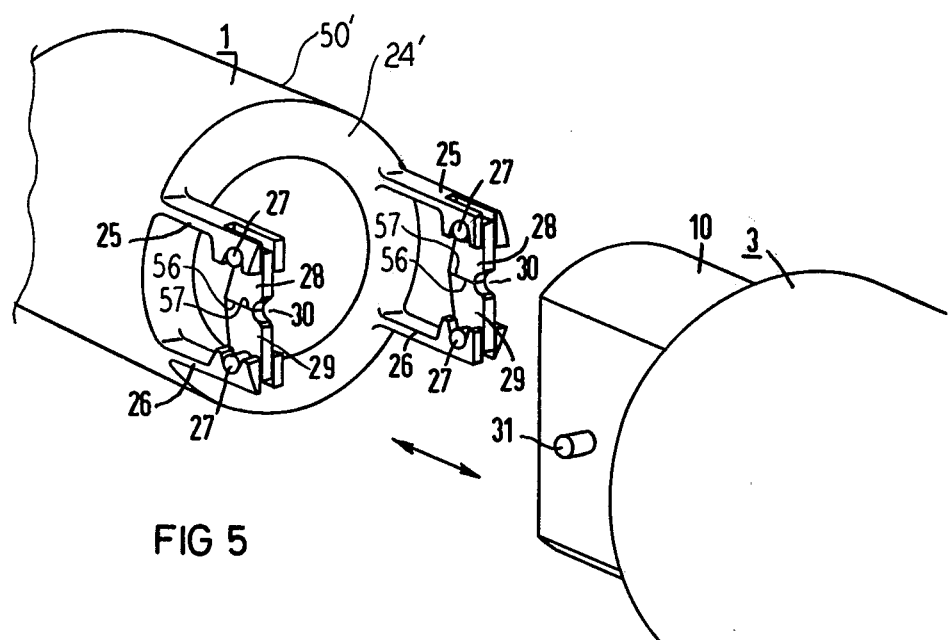
FIG. 5 is an isometric view illustrating a second embodiment of the coupling device in accordance with the present invention.
Figures 6, 7:
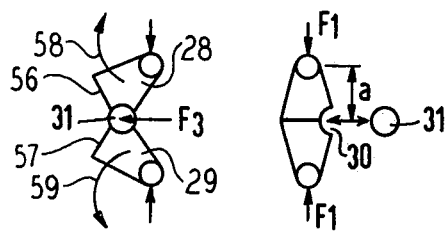
FIG. 6 is a schematic view illustrating the operation of the coupling elements while in a disconnected position.
FIG. 7 is a diagrammatic view illustrating the elements in a locked or connecting position.

Another embodiment of the means for connecting is illustrated in FIGS. 5, 6 and 7. In this embodiment, a pair of bridge arms 25 and 26 extend from the end 24' of a member 50' of the grip section 1, which as the outer sleeve removed. As illustrated, two pairs of arms are provided and each of the bridge arms 25 and 26 are constructed as leaf spring elements. Extending between the two arms are two laminae or levers 28 and 29 which are arranged with pivot pins 27 rotatably seated in groove-like seats formed on the ends of the arms 25 and 26. Each of the two levers 28 and 29 have a triangular configuration and form a one side lever with the lever 28 having an end surface 56 engaging an end surface 57 of the lever 29. Adjacent the engaged end surface 56 and 57, the levers are provided with recesses to coact to form a recess 30, which is approximately half the circumference of a guide pin 31 mounted on the projection 10 of the part 3. In an unlocked position or disconnected position (FIG. 6), a vertical force $F_1$ is applied to the two levers 28 and 29 by the leaf spring elements or arms 25 and 26 so that the surfaces 56 and 57 are in tight engagement. When the pin 31 is pressed into the recess 30 due to axial placement of the head part 3 into the grip section 1, each of the recesses forming the recess 30 move in an arc indicated by the arrows 58 and 59. It should be noted that the initial movement of the pin 31 to cause the levers to move along the initial portion of the arc will be opposed by the force $F_1$. However, after the parts have moved a sufficient amount along the arc, the force $F_1$ will create a force $F_3$ urging additional movement to bring the two parts 3 and 50' into connection. As in the previous embodiment, the parts 3 and 50' will move axially until an abutting stop surface, such as an end of the projection 10 abutting on the end surface 24' of the member 50' occurs. To disengage the two parts only the returning force $F_3$ must be overcome.

If sufficient space is available, the arrangement can also be provided in which the arms 25 and 26 are rigid and tension springs act on the levers 28 and 29. The springs are arranged so that after a certain movement from the position illustrated in FIG. 5, the spring force acts to cause continued rotation of the levers in the direction of arrows 58 and 59.

Both of the embodiments of the connection means utilize elements, which will assume two definite positions so that in an unlocked or disconnected position, a force will generally attempt to push the two parts apart until the elements have moved beyond a dead center point or position at which time the resilient force acts to urge the parts towards the final connecting position. Thus, after passing the over center point, the resilient force acts to frictionally force the parts together to form the lock-in mechanism.

A significant advantage of the invention of the lock-in mechanism is that no axial excess stroke is required for connecting the parts. This advantage is particularly useful in a dental handpiece constructions whose interior drive shafts are arranged to mesh precisely with one another. However, the employment of this snap-in or lock-in mechanism described above is not limited to handpiece parts which were described in the sample embodiments. It can also may be employed for the connection of other handpiece parts or for connecting a hose connection to the handpiece.

Although various minor modifications may be suggested by those versed in the art, it should be understood that we wish to embody within the scope of the patent granted hereon, all such modifications as reasonably and properly come within the scope of our contribution to the art.

We claim:

1. A device for releasably connecting two parts of a dental handpiece together comprising coacting means being provided on the two parts for preventing twisting between said parts and for guiding said parts on a path from a beginning of a connection until stop surfaces of said parts abut to define a final connecting position, said coacting means having at least one axial guidance surface; and connecting means for releasably holding the two parts together in the final connecting position including at least one pair of coacting connecting elements mounted on said parts, one connecting element of each pair having an engagement surface for engaging the other element of the pair and being mounted for rotation on one part with said engaged surface moving in an arc between an unlocked position and a position at which the two parts are in the final connecting position and said connecting means including resilient means for each pair of elements acting on said one element to urge said engagement surface along said arc at least during the last part of travel towards the connecting position so that said two parts are held in the final connecting position by the resilient means acting on the one element of the connecting means.

2. A device according to claim 1, wherein the one element comprises a coupling lever having a pin spaced from the point of mounting and the other element comprises a slot in the other part, said slot having at least one portion extending at an angle to the path of movement of the parts during a connection so that the pin moving in said slot is rotated in an arc.

3. A device according to claim 1, wherein the one element is formed by a plate having an engagement surface formed by a recess and the other element is a pin fixedly mounted on the other part, said movement of the pin engaging the recess during coupling causing the plate to rotate to a locking position.

4. A device according to claim 1, wherein the one element of each pair has a configuration coacting with the resilient means, and said resilient means opposing a movement of the engagement surface from the unlocked position so that during travel from the unlocked to the locked position, an over center arrangement is obtained.

5. In a device according to claim 4, wherein the one element is a plate mounted for rotation on an axle and said engagement surface is a pin displaced from the axle, said plate having a surface engaging the resilient means, the other element of each pair being a slot disposed in the other part and having at least one portion extending at an angle to the direction of movement of said parts during a connecting operation.

6. In a device according to claim 5, wherein said plate has at least two sides merging to form a high point, one of said two sides being initially engaged by the resilient means while the element is in the unlocked position, said resilient means opposing initial rotation of the plate during a connecting operation until the high point passes through a given arc at which time the resilient means urges continued rotation, said slot having a configuration to initially urge rotation of the pin about the axle against the spring during initial portion of the connection position.

7. A device according to claim 1, wherein the one element comprises a disc having a pin extending therefrom, said disc being mounted on one part by an axle eccentrically disposed to the axis of the pin, said resilient means being a spring loaded thrust bolt acting against a narrow surface of said disc, and the other coupling element being a slot in the other part receiving said pin and causing rotation of the pin about said axle.

8. A device according to claim 7, wherein said slot has an initial portion receiving said pin without imposing rotation thereto and a second portion extending at an angle to the path of movement to cause rotation against the spring loaded thrust bolt until said plate moves through an over center position to have the spring loaded thrust bolt urge continued rotation to the locked position.

9. A device according to claim 7, wherein the slot has an initial portion extending parallel to the axis of symmetry of said part and has a second portion having a side wall extending at acute angle to the axis of symmetry, said side wall causing the rotation of the plate to move the engagement surface in said arc.

10. In a device according to claim 1, wherein the one connecting element of each pair is a pair of coacting levers each mounted for rotation with an end surface in engagement with each other and disposed between the mounting points, said engagement surface being formed by a recess in the pair of levers adjacent the engaged end surfaces and said resilient means acting on each lever, said other element of each pair of connecting elements being a pin fixedly mounted on the other part and engaged in the recess formed by the pair of levers so that initial rotation of the levers during initial coupling is opposed by the resilient means until the point of engagement between the two levers moves through an over center position.

11. In a device according to claim 10, wherein the resilient means are provided by a pair of resilient arms extending from said part and each of said arms having means for mounting one of said levers.

12. In a device according to claim 1, wherein said two parts comprises a head part and a grip section of the dental handpiece.

13. A device according to claim 1, wherein the connecting means includes two pairs of connecting elements disposed on opposite sides of the axes of the parts.

* * * * *